United States Patent [19]

Hammermeister

[11] Patent Number: 5,541,856
[45] Date of Patent: Jul. 30, 1996

[54] X-RAY INSPECTION SYSTEM

[75] Inventor: David W. Hammermeister, Madison, Wis.

[73] Assignee: Imaging Systems International, Madison, Wis.

[21] Appl. No.: 148,801

[22] Filed: Nov. 8, 1993

[51] Int. Cl.$^6$ .................................................. G01B 15/08
[52] U.S. Cl. .................. 364/552; 364/516; 364/551.01; 324/501; 378/196; 378/198; 378/205; 378/58; 382/145; 382/151; 382/152
[58] Field of Search ..................................... 364/516, 550, 364/551.01, 552; 324/501; 348/126; 382/8, 145, 151, 152; 378/193, 195–197, 205, 58, 177, 167

[56] References Cited

U.S. PATENT DOCUMENTS

| | | | |
|---|---|---|---|
| 3,809,886 | 5/1974 | Cochran et al. | 250/323 |
| 3,890,552 | 6/1975 | Devol et al. | 378/197 |
| 4,210,815 | 7/1980 | Riehl | 378/196 |
| 4,211,927 | 7/1980 | Hellstrom et al. | 378/197 |
| 4,356,400 | 10/1982 | Polizzi et al. | 378/205 |
| 4,809,308 | 2/1989 | Adams et al. | 378/58 |
| 4,926,452 | 5/1990 | Baker et al. | 378/22 |
| 5,023,899 | 6/1991 | Ohlson | 378/196 |
| 5,048,070 | 9/1991 | Maehama et al. | 378/193 |
| 5,164,974 | 11/1992 | Kariya et al. | 378/205 |
| 5,315,630 | 5/1994 | Sturm et al. | 378/205 |

FOREIGN PATENT DOCUMENTS 58340  3/1913  Germany ................................ 378/196

OTHER PUBLICATIONS

*Nicolet Realtime X–Ray Imaging Systems, A Quality Investment in PCB Fabrication*, Nicolet Measurement Instruments, Madison WI, admitted Prior art.
*Realtime X–ray Imaging Applications, Ensuring Quality in IC Packaging*, Nicolet Test Instruments, Madison WI, admitted prior art.
*The Nicolet NXR 1400 Real Time X–Ray Imaging System*, Nicolet Test Instruments, Madison WI, admitted prior art.
*NXR1001*, Nicolet Measurement Instruments, Madison, WI Feb. 1992.
*NXR Accessory*, Nicolet Test Instruments, Madison WI, admitted prior art.

Primary Examiner—Ellis B. Ramirez
Assistant Examiner—Kyle J. Choi
Attorney, Agent, or Firm—Quarles & Brady

[57] ABSTRACT

An x-ray inspection machine particularly suited for use on an assembly line has a narrow footprint produced by mounting opposed x-ray tube and camera on independently movable stages locked together by way of a central computer rather than a physical member. The stages are aligned by using position sensors at home positions and a fiduciary mark on the part to be inspected. The independent motion of the stages permits a limited range of angled inspections to be obtained without additional angulation mechanisms.

12 Claims, 3 Drawing Sheets

X-RAY INSPECTION SYSTEM

FIELD OF THE INVENTION

The present invention relates to inspection equipment and more specifically to an x-ray inspection machine suitable for use in an assembly line or the like.

BACKGROUND ART

In the assembly of some products, it is necessary to inspect the product at a stage in the assembly when the elements to be inspected are hidden from the human eye or a machine vision inspection system. For example, the solder joints attaching some high density integrated circuits to a circuit board can be inspected only after the integrated circuits are in place covering the joints to be inspected.

In such circumstances, an x-ray inspection system may be used. Typically such a system employs an x-ray source, opposing a detector about the part to be inspected. The x-ray source is normally an electron tube accelerating electrons in a vacuum from a cathode to a fixed anode as focussed by one or more focussing grids. The x-ray radiation penetrates any obscuring structure to produce a shadow image or radiograph of the part from which the desired elements may be discerned as variations in x-ray attenuation. For example, a metallic solder joint may be detected as a region of high attenuation contrasting with the uniform and frequently lesser attenuation of the obscuring integrated circuit package and die.

In addition to the usefulness of x-rays in penetrating the obscuring outer structure of a part, x-ray inspection systems are ideally suited to the inspection of extremely small features, such as the bonding wires and an integrated circuit. The short wave-length of x-ray emissions, the ability to produce in the x-ray source an extremely small (0.01 mm) focal spot from which the x-rays emanate, and the simple geometry of an opposed x-ray source and detector permit the ready production of high quality, highly magnified images. The magnification is dependent on the ratio of the separation between the x-ray source and the part, compared to the separation between the x-ray source and the x-ray detector. As the detector is moved further from the point source, provided the part remains stationary, the image size is increased in much the same way as a shadow cast on a distant wall is bigger than a shadow cast on a closer wall. Magnifications of greater than 100:1 are routinely obtained.

The high degree of magnification provided by such x-ray inspection systems requires that the camera, the x-ray source, and the part to be inspected be precisely and stably located with respect to each other. Misalignment by amounts as little as 0.0000492 inches can adversely affect the accuracy of the inspection, particularly where the inspection is performed by a machine vision system which is less accommodating to misalignment error than is a human operator.

The necessary stability and accuracy is normally obtained by rigidly mounting the camera and x-ray source to the frame of the inspection system and separately moving the part to be inspected as precisely located, by registration pins, for example, on a table tied to the same frame by an indexing mechanism.

A rigid mounting of the x-ray source is also undertaken to reduce any physical shock to the x-ray source which may adversely affect the size of the x-ray source's focal spot. Thermal variation are reduced by leaving the x-ray source on at all times. The small focal spot of the x-ray source (less than one-hundredth the diameter of a typical medical x-ray source) is necessary to eliminate a penumbra that may blur a highly magnified image and is accomplished by multiple focussing grids and a special x-ray source anode geometry.

Originally, x-ray inspection systems were used for spot inspections of manufactured parts by a human operator. Nevertheless, with improvements in machine vision techniques, the potential exists for automated inspection of 100% of a production run. Unfortunately, current bulky x-ray inspection systems are not well suited for modern factories where space is at a premium. Also, the need to individually locate each part precisely with respect to the x-ray source and camera, by registration pins or the like, is counter to the high throughput required of a 100% inspection system.

SUMMARY OF THE INVENTION

The present invention provides an x-ray inspection system suitable for the high production rates normally found on assembly lines and having a reduced size compatible with the space demands of a modern factory.

Generally, the x-ray source and camera, rather than being fixed to a common frame are mounted on individual stages capable of independent movement. This provides a significantly reduced width to the inspection system permitting it to be integrated along a standard conveyor line. An automated alignment procedure ensures the initial alignment of the two stages. The automated alignment procedure may include alignment to fiducial marks on the part being inspected, eliminating the need for accurate mechanical registration of the part prior to inspection, thus increasing the inspection system's throughput.

Specifically, the inspection system includes a parts carrier that may transport a part to be inspected along a conveyor axis to an inspection position. The part has a width measured along a transverse axis perpendicular to the conveyor axis of less than a predetermined maximum board width. An x-ray source is mounted on a first stage to direct a beam of x-rays across the inspection position along a beam axis orthogonal to the conveyor axis and the transverse axis. The first stage, which may be positioned at a number of positions along the transverse axis, is connected with a first position sensor which produces a home signal when the first stage is in a home position. The x-ray source is mounted so as to present a width along the transverse axis much less than the maximum board width.

A second stage independently positionable along the transverse axis communicates with a second position sensor which produces a home signal when the second stage is in a second home position. An x-ray camera is mounted to the second stage to receive a beam of x-rays across the inspection position along an axis substantially parallel to the beam axis.

The x-ray camera produces an image that is received by an electronic computer, the latter which is also connected to motors and encoders for moving the first and second stages and the parts carrier under control of the computer. The electronic computer receives the home signals from the position sensors and operates according to a stored program to move the part along the conveyor axis to the inspection position. The two independently movable stages are then coordinated electronically by moving the first and second stages to their home positions and only then to an inspection position predetermined distances from the home positions.

At the inspection point, the computer analyzes the image formed by the camera to determine whether the part conforms to a parts standard and displays an indication of whether the part conforms to the part standard.

It is thus one object of the invention to provide a compact x-ray inspection system retaining the accuracy necessary for automated inspection at high magnifications. By mounting the x-ray source and camera separately, no connecting structure, such as a C-arm, is needed and thus the entire inspection system may have a width not much more than the width of the part to be inspected. In contrast, the use of a C-arm type structure or moving the part with respect to the x-ray source and camera mounted on a single frame, would require a width of at least twice that of the part to be inspected. Errors in tracking, between the independent x-ray source and the camera are rendered acceptable by use of a homing procedure in which the camera and x-ray source are positively located at a home position provided by a position sensor.

The first and second predetermined distances may be different so as to intentionally change the alignment of the x-ray source and camera.

Thus it is another object of the invention to exploit the independent mounting of the x-ray source and camera to provide a simple method of obtaining an angled view of a part such as may reveal additional information as to possible defects.

The part may also include a fiduciary mark at a fiduciary position, the mark being detectable by x-ray inspection and being in a predetermined known position. The electronic computer may include a program for moving the first and second stages to the fiduciary position after the home position and for analyzing the part at the fiduciary position and detecting the fiduciary mark so as to generate a correction factor. The correction factor may be used to more accurately locate the part at the inspection position.

Thus it is a further object of the invention, to increase the inspection systems' accuracy in co-locating an independently movable x-ray source and camera by using a fiduciary mark on the part to be inspected and analyzing that mark to determine possible errors in the positioning of the camera and x-ray source with respect to the part. The use of an on-part fiduciary mark also permits the elimination of registration pins or other similar mechanical restraints for holding the part, rendering the inspection system conducive to the use of conventional conveyor transportation mechanisms which may be faster but which provide much less accuracy in the location of the part. An image based alignment system insures precise location of the separately movable components and permits elimination of additional registration mechanisms.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
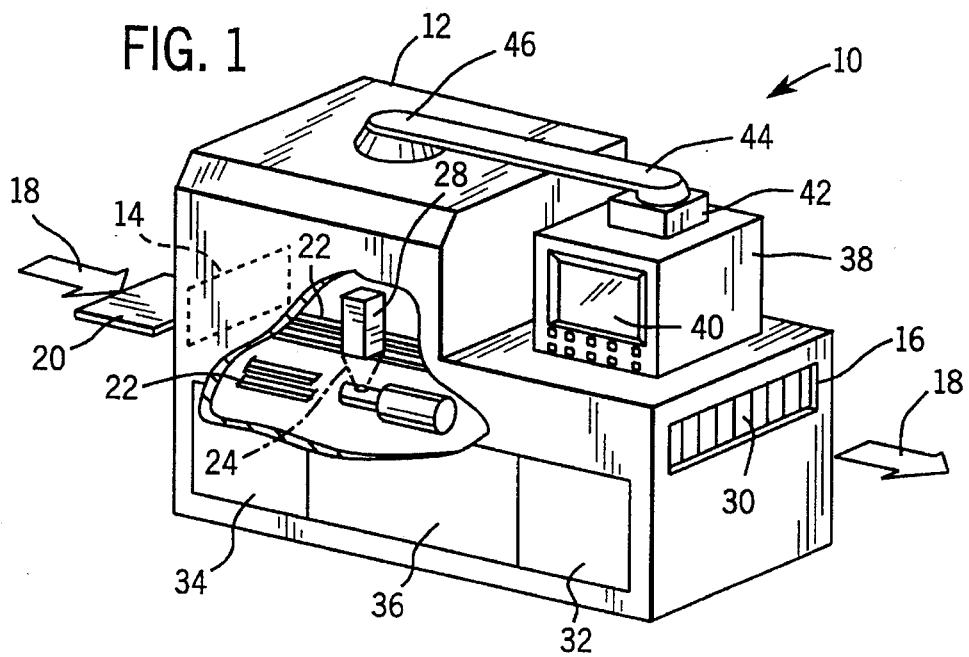
FIG. 1 is a perspective view of an x-ray inspection system of the present invention in partial cut away showing the conveyor axis and the x-ray source and camera.

Referring to FIG. 1, an x-ray inspection system 10 includes a shielding cabinet 12 having an entrance port 14 and an exit port 16 being rectangular apertures disposed in a straight line along a conveyor axis 18 at opposite sides of the cabinet 12. Exit and entrance ports 14 and 16 include lead curtains 30 to minimize the passage of scattered x-rays outside of the cabinet 12.

A part 20, to be inspected, enters the cabinet 12 through the entrance port 14 along the conveyor axis 18 and is carried by conveyor 22 to an inspection position within the cabinet 12 to be illuminated by an x-ray beam 24 produced by an x-ray tube 26 to pass through the part 20 and be received by an x-ray camera 28. The part 20 may then continue along conveyor 22 and passes out of exit port 16. Alternatively, the conveyor 22 may be reversed in direction and the board may be ejected out of entrance port 14 in the opposite direction in which it was inserted.

X-ray power and control circuitry 32 is provided in the base of the cabinet 12 and supplies the high voltage electricity needed to operate the x-ray tube 26 as is well understood in the art. Also held in the base of the cabinet 12 are conventional motor interface electronics 34 for controlling various motors, such as the motor operating the conveyor 22, as will be described further below.

A computer 36 communicates with the x-ray power and control circuitry 32 and the motor interface electronics 34 so as to coordinate the motion of the conveyor 22, the camera 28 and the x-ray tube 26 and to turn the x-ray tube 26 on and off according to a stored program as will be described. The computer 36 is a conventional microprocessor based system employing a 486 microprocessor available from Intel Corporation of California, and incorporates a video interface card for receiving an image in digital form from the camera 28 according to techniques well known in the art. The computer 36 also includes a video image processor such as that commercially available from Pattern Processing Technologies of Eden Prairie, Minn. under the tradename of 400 VPC.

The computer 36 also communicates with a monitor/control panel 38 having a display screen 40 for receiving control information and for displaying the image developed by camera 28 and indicating the result of any analysis of that image with respect to possible defects in the part 20. The monitor/control panel 38 hangs from a swivel bearing 42 attached to one end of a cantilevered beam 44 mounted by means of a second swivel bearing 46 to the top of the cabinet 12 so that the monitor/control panel 38 may be swung to a convenient position away from the path of flow of parts 20 along conveyor axis 18.

Figure 2:
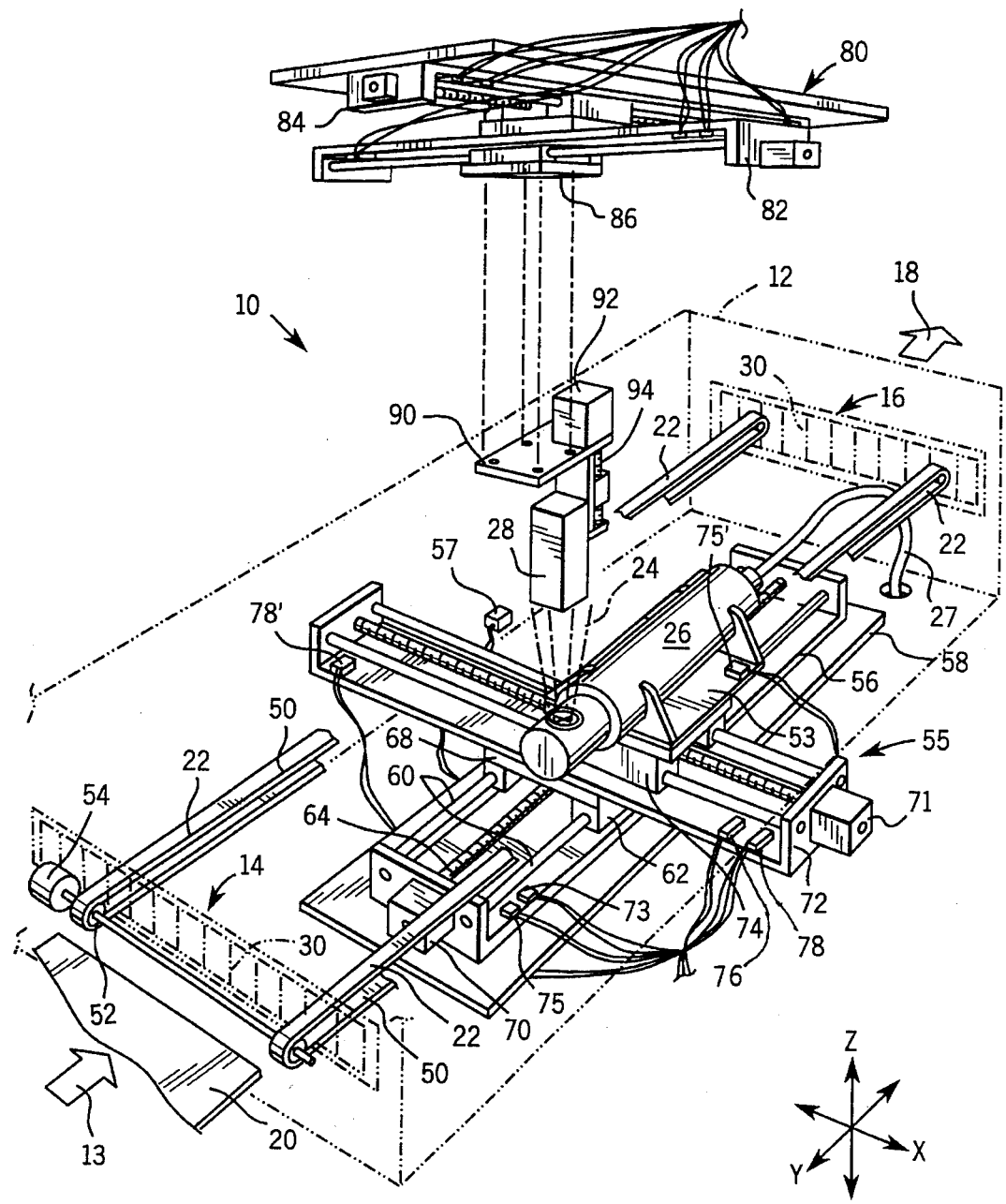
FIG. 2 is an exploded perspective view of independently movable stages on which the x-ray source and camera of FIG. 1 are mounted.

Referring now to FIG. 2, the conveyor 22 comprises two conveyor belts 50 extending from the entrance port 14 to the exit port 16 and flanking the conveyor axis 18 through the center of the cabinet 12. The conveyor belts 50 support the part 20 (typically a circuit board) at its edges and carry along the conveyor axis as driven by belt wheels 52 via reversible motor 54. The motor 54 is controlled in speed and direction by the computer 36 shown in FIG. 1. A board sensor 57, placed along the conveyor 22, provides a signal to computer 36 stopping the motion of the motor 54 when the part 20 is positioned in an inspection position where it may be exposed by the x-ray beam 24 with various motions of the camera 28 and x-ray tube 26 as will be described.

Beneath the conveyor 22 and generally positioned between the conveyor belts 50 in the inspection position is the x-ray tube 26. The x-ray tube 26 comprises generally an elongate evacuated cylinder mounted so that its longest dimension is along the conveyor axis 18 and it shortest dimension is perpendicular to conveyor axis 18 along a transverse axis. A high voltage cable 27 extends along the conveyor axis 18 to the x-ray power and control circuitry 32 and to provide freedom of movement of the x-ray tube 26 without undue flexure of the cable 27.

A conical x-ray beam 24 projects upward from the x-ray tube 26 and has its apex at a focal spot (not shown in FIG. 2) on an anode of the x-ray tube 26. The x-ray tube 26 is a stationary anode design employing a series of focus grids to produce an extremely small focal spot on the order of 0.1 mm.

The conveyor axis 18 and the transverse axis may be described, respectively, by a y and x coordinate of a Cartesian coordinate system and the axis of the conical x-ray beam 24 by the z-axis of that system. The x-ray beam 24 thus projects upward along a z-axis where it may intersect the part 20 held by the conveyor 22. After passing through the part 20, the x-ray beam 24 is received by camera 28.

The x-ray tube 26 is carried on an x-y stage 55 for moving the x-ray tube 26 generally within the y-x plane relative to the cabinet 12. The x-ray stage 55 includes a first carriage 56 attached to the cabinet 12 via platform 58. The carriage 56 includes two cylindrical ways 60 along which sliding bearing blocks 62 move driven by a lead screw 64 positioned between the ways 60. The sliding bearing blocks 62 and a lead screw nut (not shown) are attached to a rider platform 68 which moves along the y-direction with rotation of the lead screw 64. The lead screw 64 is rotated by stepping motor 70 attached at one end of the carriage 56.

Positioned along the carriage 56 are a home sensor 73 and a limit sensor 75 which may sense the presence of the rider platform 68 at a corresponding home position and a limit position 75, both being near one end of the carriage 56 with the latter corresponding roughly to the limit of travel of the rider platform 68 on the ways 60. The limit and home sensors, 75 and 73, provide signals to the computer 36 indicating the location of the rider platform 68 along the carriage 56. A second limit sensor 75' is positioned at the opposite end of the carriage 56 from limit sensor 75.

On the top surface of the rider platform 68 is mounted a second carriage 72 corresponding almost identically to carriage 56 but positioned at right angles to move its rider platform 74 along the x-axis under the control of motor 71. Importantly, the overall length of the second carriage 72 along the x-axis is nearly equal to the width of the widest part 20 anticipated to be placed through entrance port 14 for inspection by the inspection system 10 and significantly less than twice that width. Atop of the rider platform 74 of the second carriage 72 rests a cradle 53 supporting the x-ray tube 26. Thus the x-ray tube 26 may be moved so that the x-ray beam 24 illuminates an arbitrary portion along the full width of the widest part 20 anticipated to be placed on the conveyor 22.

Like carriage 56, the second carriage 72 has a home sensor 76 and a limit sensor 78, the limit sensor 78 being placed near one extreme end of the second carriage 72 and corresponding approximately to the limit of travel of the rider platform 74. Again, a second limit sensor 78' provides a limit indication for movement toward the opposite end of the second carriage 72.

A second, independently movable stage 80, of similar construction to stage 55, is positioned above the conveyor 22 for holding the camera 28. This second stage 80 includes first and second perpendicularly extending carriages 82 and 84, each having a lead screw for moving its respective rider platform, and producing a net motion on a lower most rider platform 86 within an x-y plane. Each carriage 82 and 84 includes limit and home sensors functionally identical to those described with respect to carriage 56 and 72 and connected with computer 36 to provide positive information as to at least one position of the rider platform 86.

Mounted to the lower surface of rider platform 86 is a z-axis carriage 90 having a motor 92 and lead screw 94 for moving the camera 28 up or down along the z-axis between approximately 5 cm and 25 cm from the x-ray tube 26. Home and limit sensors (not shown) similar to sensors 73 and 75 and 75', provide signals to computer 36 indicating that the camera 28 is in a home or limit position along the z-axis. The motor 92 is also controlled by the computer 36.

In the preferred embodiment, the motors of the carriages 56, 72, 82, 84 and 90 are stepper motors operated according to methods well known in the art and including incremental encoders indicating the actual stepping of the motors. Each step of these motors, as commanded by the computed 36, moves the camera 28 or x-ray tube 26 by a predetermined amount determined by the pitch of the motor's attached lead screw, the direction of the carriage, and verifiable by the motor's encoder. Hence, once a single position of the camera 28 or x-ray tube 26 is determined, subsequent positions may be deduced by counting the steps since that position. The initial position is determined by a homing sequence to be described.

It will be recognized, however, from the following discussion, that any general purpose motor may be used provided a position signal is developed to positively identify at least one position of the camera 28 and the x-ray tube 26 to the computer 36.

The limit sensors in the preferred embodiment are reed switches activated by magnets attached to the lead screw nuts. However, for motor types other than stepper motors, other position sensors may be preferred to provide the absolute indication of motor position. In this case, the home position may be any position that may be absolutely verified by a signal received by the computer 36.

Mounting the camera 28 and x-ray tube 26 on independently movable stages, having no direct physical connection, significantly reduces the width of the x-ray inspection system 10. If the camera 28 and x-ray tube 26 were connected by a rigid structure such as a "C-arm", the vertical portion of the arm would have been displaced by at least one part width from the center of the x-ray beam 24 so that the far edge of the part 20 could be inspected. This would mean that the vertical portion of the C-arm would extend by at least a part width in the x direction from the edge of the part 20 when the opposite edge of the part 20 were being inspected. The same problem occurs in directly mounting the x-ray tube 26 and camera 28 on the frame of the cabinet 112 where the cabinet 12 acts as the C-arm.

In contrast, in the present invention, the stepper motors and sensors together form a virtual electric connection between the x-ray tube 26 and camera 28, a connection which having no physical extent, does not increase the width of the x-ray inspection system.

The tradeoff for adopting a virtual electric connection in the high accuracy environment of x-ray inspection, is that a method must be provided for insuring precise alignment of the now movable x-ray tube 26 and camera 28.

Figure 3:
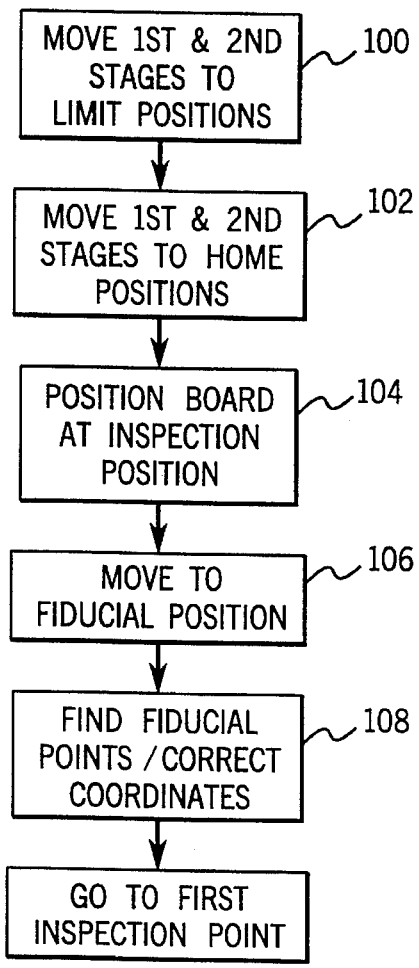
FIG. 3 is a flow chart of the operation of the inspection system of the present invention in locating the x-ray source and camera.

Referring now to FIGS. 2 and 3, alignment of the camera 28 and the x-ray tube 26 is performed in several steps. First, as indicated by process block 100, the first and second stages 55 and 80 are moved so that each of their carriages 56, 72, 82, and 84 is in the limit position near the home position. For stage 55, this will mean that rider platform 74 is at one end of second carriage 72 and rider platform 68 is at one end of carriage 56. This is performed under computer control 36 by turning each of the motors of the respective stages 80 and 55 in a predetermined direction towards the limit positions until a limit signal is received from the respective sensor.

Once the necessary limit signals are received, each of the motors is reversed in direction until the home position is sensed. This direction reversal serves to remove the effect of any backlash in the lead screws of the carriages as might affect the actual position of the x-ray tube 26 and camera 28. When the limit signals are received, the motors are stopped and the position of the camera 28 and x-ray tube 26 is set to an origin of x=0, y=0, z=0.

If limit signals or home signals are not received in process blocks 100 or 102 within a predetermined time, it is assumed that one of the sensors is defective and the sequence stops and a diagnostic indication is presented on screen 40 of monitor/control panel 38.

If process block 102 is successfully completed, the program moves to process block 104 in which the computer 36 activates motor 54 controlling conveyor 22 to move the part 20 to the inspection position as determined by sensor 57. That is, when a signal is received from sensor 57, the conveyor 22 is stopped.

Generally, the positioning of the part 20 on the conveyor 22 is not suitably precise for the high accuracy measurements made by the x-ray inspection system. This is both because a high degree of magnification may be used in the x-ray inspection system and also because variations in the magnified field of view may cause erroneous analysis of the portion of the board to be inspected by the machine vision system. For example, if solder bridges are to be detected simply by determining the average density of the image of the board at a certain location, a mis-registration of the board which puts additional solder pads into the imaged area may falsely trigger rejection of the part.

Figure 5:
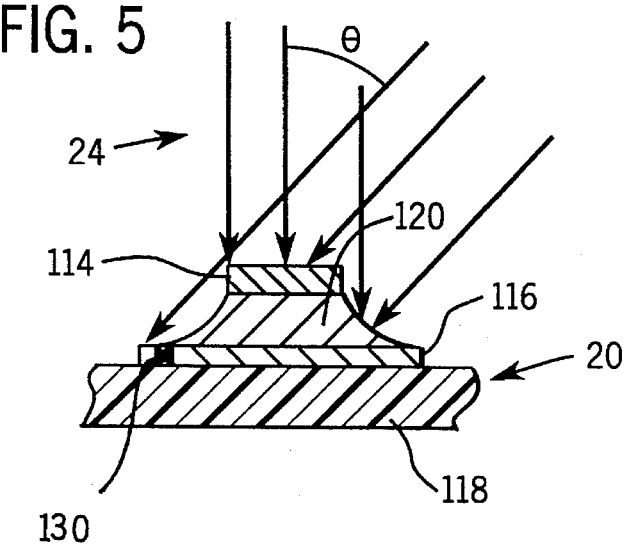
FIG. 5 is a detailed cross-sectional view of a part receiving x-rays both normal to its surface and obliquely as provide in FIG. 5.

For this reason at process block 106, both the camera 28 and X-ray tube 26 are then moved to a fiduciary position corresponding roughly to the location of a fiduciary mark on the part 20 to be inspected. Referring also to FIG. 5, the fiduciary mark may be, for example a plate-through hole 130 that is readily detected by machine vision and is isolated from other elements of the board.

Additional motion of the x and y carriages for both the x-ray tube 26 and x-ray camera 28 are made to center the fiduciary mark within the field of view. This centering is under the control of the computer 36 and may be accomplished, for example, by dividing the image received from camera 28 into four equal quadrants and making x and y motions to equalize the density of the image in each quadrant until the mark is centered. Each stage may be moved independently, that is by different amounts and different directions.

Once this centering is accomplished, the coordinates of the camera 28 and x-ray tube 26, as determined by the computer 36 having tracked the motion since the home position, are adjusted to equal the known coordinates of this fiduciary mark or more simply to a new origin of x=0, y=0.

Because the board may be tipped as well displaced in the x and y direction, that is rotated about the z-axis, a second fiduciary mark displaced from the first fiduciary mark may also be identified. This fiduciary mark is again centered within the field of view and its coordinates noted. However, these coordinates are not substituted for those then held in the computer 36. Rather, a rotation angle of the board is deduced by trigonometric formula and that a rotative angle is used to adjust the coordinates of the various inspection points to be inspected on the part 20. For example, if the second fiduciary point indicates that the board is tipped by two degrees about the origin of the first fiduciary point, each of the coordinates of the inspection points is rotated by a similar 2° about the first fiduciary point.

At the completion of process block 108, the x-ray tube and camera 28 are moved to a first inspection point preprogrammed by the user for inspecting a particular portion of the part 20. Specifically, the coordinates of the first inspection point relative to the origin of the home positions, as previously stored in the computer 36 during programing of the inspection routine, and as now corrected by the fiducial point measurements, is used to establish the necessary motions of the camera 28 and x-ray tube 26. When the inspection point is reached, the computer 36 captures an image of the part 20 which is analyzed by the video process controller according to machine vision techniques known in the art. If the part 20 does not conform to the required programmed standards, an indication is provided on screen 40. In addition, the computer 36 may provide one or more signals to remote equipment indicating the rejection of the part 20.

This process of correcting the coordinates of the independent stages 5 and 80 is repeated for each new part 20 thus insuring both an effective registration of the part 20 with respect to the x-ray tube 26 and camera 28 and insuring alignment of camera 28 with x-ray tube 26.

Figure 4:
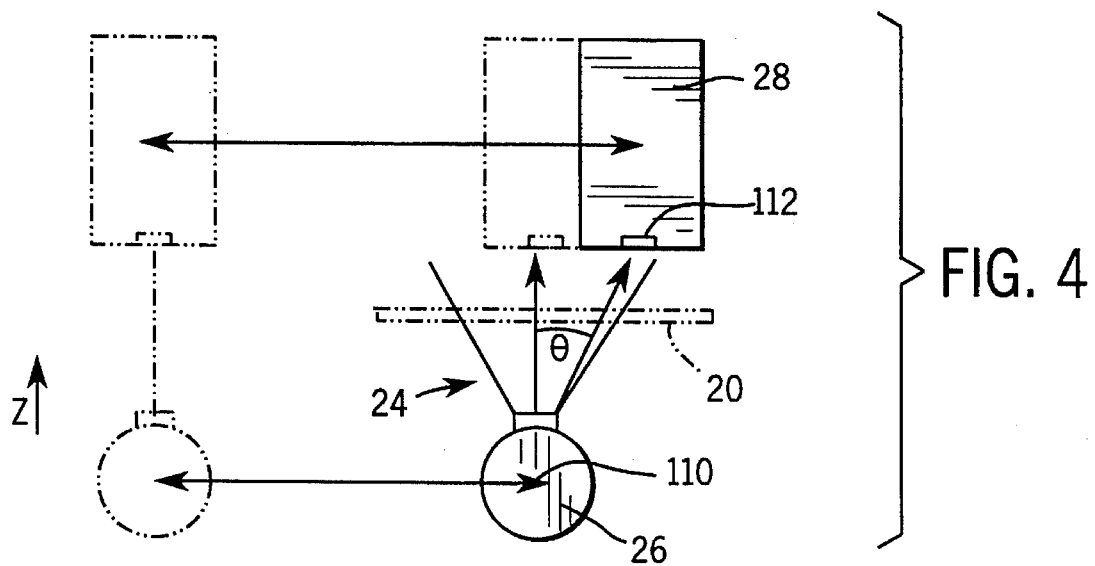
FIG. 4 is a schematic view of an x-ray source and camera as offset to provide an angled view of a part.

Referring now to FIG. 4, although it will generally be desired that the x-ray tube 26 and the x-ray camera 28 be aligned along the vertical or z-axis, the fact that both are mounted on independently movable stages provide the ability to offset the camera 28 from the x-ray tube 26 and thereby obtain oblique imaging with respect to the part 20. This occurs because the x-ray beam 24 from the x-ray tube 26 is a cone having approximately 60° apex angle representing a plurality of x-rays of diverging angles from a focal spot 110 with in the x-ray tube 26. Generally, only a portion of the cone of the x-ray beam 24 is received by an imaging aperture 112 within the camera 28 which has a diameter of 20 mm compared to the nearly 25 cm base of the cone 25 cm from the x-ray tube 26. Thus movement of the imaging aperture 112 with in the cone of x-ray beam 24 changes the angle θ of the x-rays passing through the part 20 and received by camera 28.

Referring to FIG. 5, generally it will be desired that the rays of the x-ray beam 24 impinging on a planar part 20 be normal to the surface of that part (and thus a plan view of the part 20 be obtained). For certain diagnostic tests, however rays of the x-ray beam 24 oblique to the surface of the part 20 will provide more information. For example, a lead 114 of an integrated circuit may be attached to a trace 116 on e printed circuit board 118 by means of solder 120. Viewing the trace 116 and lead 114 at an angle normal to the surface of the board 118 provides a little indication as to "wetting" of the surfaces by the solder 120 as indicated by a concave surface to the solder 120. On the other hand, tipping the angle of viewing by changing the angle of x-rays impinging on the board permits a profile of the solder 120 to be developed better providing an indication as to whether proper wicking was obtained.

The particular angle of the rays θ will depend on offset between the camera 28 and the x-ray tube 26 in the x-y plane and the separation between the camera 28 and the x-ray tube 26 in the z direction and hence may vary as a function of the magnification of the image as will be accounted for by the computer 36.

While this invention has been described with reference to particular embodiments and examples, other modifications and variations will occur to those skilled in the art in view of the above teachings. Accordingly, the present invention is not limited to the preferred embodiment described herein, but is instead defined in the following claims.

I claim:

1. An x-ray inspection system comprising:

a parts carrier transporting a part along a conveyor axis to an inspection position, the part having a width, measured along a transverse axis, perpendicular to the conveyor axis, of less than a predetermined maximum board width;

a first stage positionable along the transverse axis at a plurality of positions including a first home position;

a first position sensor producing a first home signal when the first stage is in the first home position;

an x-ray source mounted on the first stage to direct a beam of x-rays across the inspection position, the x-ray beam centered along a beam axis substantially orthogonal to the conveyor axis and transverse axis; the x-ray source mounted so that a width of the x-ray beam along the transverse axis is much less than the maximum board width;

a second stage independently positionable along the transverse axis at a plurality of positions including a second home position;

a second position sensor producing a second home signal when the second stage is in the second home position;

an x-ray camera mounted on the second stage to receive a plurality of x-rays across the inspection position to produce an x-ray image;

an electronic computer connected to separate motive means for moving the first and second stages and the parts carrier, and to the home sensors for receiving the first and second home signals, and to the camera for receiving the x-ray image, the electronic computer operating according to a stored program to control:
   (i) a first motive means for moving the part along the conveyor axis to the inspection position;
   (ii) a second motive means for moving the first and second stages to the first and second home positions respectively and moving the first and second stages a first and second predetermined distance, respectively, from the first and second home positions to an inspection position, a portion of the part on the carrier subtendable by the x-ray beam when said part is at the inspection position;

iii an analyzer to analyze the image from the camera at the inspection position to determine conformance to a parts standard; and iv a display to display an indication of whether a part conforms to a parts standard.

2. The inspection system of claim 1 wherein the first and second stages are also independently positionable along the conveyor axis.

3. The inspection system of claim 1 wherein at least one of the first and second stages are independently positionable along an axis parallel to the beam axis.

4. The inspection system of claim 1 wherein the first and second predetermined distances are equal.

5. The inspection system of claim 1 wherein the first and second predetermined distance differ by an amount dependent of the separation of the x-ray source and camera.

6. The inspection system of claim 1 wherein the third and fourth predetermined distance differ by an amount dependent on the separation of the x-ray source and camera.

7. The inspection system of claim 1 wherein the x-ray beam is a conical fan x-ray beam including a plurality of x-rays diverging at various angles from a focal spot, the fan beam centered on the beam axis.

8. The inspection system of claim 7 wherein the first and second predetermined distances differ so that the plurality of x-rays received by the camera diverge from the x-ray beam axis.

9. An x-ray inspection system for a part having a fiducial mark at a fiducial position, the mark being detectable by x-rays and being in a predetermined known position, the inspection system comprising:

a parts carrier transporting a part along a conveyor axis to an inspection position, the part having a width, measured along a transverse axis, perpendicular to the conveyor axis, of less than a predetermined maximum board width;

a first stage positionable along the transverse axis at a plurality of positions including a first home position;

an x-ray source mounted on the first stage to direct a beam of x-rays across the inspection position, the x-ray beam centered along a beam axis substantially orthogonal to the conveyor axis and transverse axis; the x-ray source being so mounted to present a width along the traverse axis much less than the maximum board width;

a second stage independently positionable along the transverse axis at a plurality of positions including a second home position;

an x-ray camera mounted on the second stage to receive a plurality of x-rays across the inspection position along and axis substantially parallel to the beam axis and to produce an x-ray image;

an electronic computer connected to separate motive means for moving the first and second stages and the parts carrier, and to the camera for receiving the x-ray image, the electronic computer operating according to a stored program to control:
   (i) a first motive means for moving the part along the conveyor access to the inspection position;
   (ii) a second motive means for moving the first and second stages to the first and second home positions respectively and moving the first and second stages a first and second predetermined distance, respectively, from the source and camera home positions to a fiducial mark position;
   iii an analyzer to analyze the image from the camera at the fiducial position to determine a correction factor based on the location of the fiducial mark;

iv a third motive means for moving the first and second stages a third and fourth predetermined distance as modified by the correction factor to a inspection position, a portion of the part on the carrier subtendable by the x-ray beam when said part is at the inspection position;

v a second analyzer to analyze the image from the camera at the inspection position to determine conformance to a parts standard; and vi a display to display an indication of whether a part conforms to the parts standard.

10. The inspection system of claim 9 wherein the first and second stages are also independently positionable along the conveyor axis.

11. The inspection system of claim 9 wherein at least one of the first and second stages are independently positionable along an axis parallel to the beam axis.

12. The inspection system of claim 9 wherein the third and fourth predetermined distances are equal.

* * * * *